(12) United States Patent
Schinski et al.

(10) Patent No.: US 6,380,420 B1
(45) Date of Patent: Apr. 30, 2002

(54) PROCESS FOR MAKING FATTY ACID NITRILES AND FATTY AMINES BY CROSS-METATHESIS OF NORMAL ALPHA OLEFINS

(75) Inventors: William L. Schinski, San Rafael; Michael S. Driver, San Francisco, both of CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 09/657,859

(22) Filed: Sep. 8, 2000

Related U.S. Application Data

(60) Provisional application No. 60/219,080, filed on Jul. 18, 2000.

(51) Int. Cl.[7] ............................................. C07C 209/48
(52) U.S. Cl. ....................... 558/308; 558/357; 558/457; 558/462; 564/490; 564/491; 564/492; 564/493
(58) Field of Search .................................. 558/308, 357, 558/457, 462; 564/490, 491, 492, 493

(56) References Cited

U.S. PATENT DOCUMENTS

| | | | |
|---|---|---|---|
| 3,574,754 A | 4/1971 | Specken | 260/583 |
| 4,681,956 A | 7/1987 | Schrock | 556/12 |
| 4,727,215 A | 2/1988 | Schrock | 585/645 |
| 5,142,073 A | 8/1992 | Schrock et al. | 556/57 |
| 5,146,033 A | 9/1992 | Schrock et al. | 585/647 |
| 5,175,370 A | 12/1992 | Fruth et al. | 564/493 |

OTHER PUBLICATIONS

Database CAPLUS on STN, Acc. No. 1996:683340, Olivier et al., 'Nonaqueous room–temperature inonic liquids: a niw class of solvents for catalytic organic reactions.' Chem. Ind. (Dekker), 1996, 68 (Catalysis of Organic Reactions), pp. 249–263.*

Crowe et al., "Acrylonitrile Cross Metathesis: Coaxing Olefin Metathesis Reactivity from a Reluctant Substrate", J. Am. Chem. Soc., 117, 5162–5163 (1995).

* cited by examiner

*Primary Examiner*—Brian J. Davis
(74) *Attorney, Agent, or Firm*—James W. Ambrosius; W. K. Turner

(57) ABSTRACT

A process for preparing fatty amines by the cross-metathesis of normal alpha olefins and acrylonitrile to form an intermediate fatty acid nitrile which is hydrogenated to the corresponding fatty amine.

25 Claims, No Drawings

PROCESS FOR MAKING FATTY ACID NITRILES AND FATTY AMINES BY CROSS-METATHESIS OF NORMAL ALPHA OLEFINS

CROSS-REFERENCE TO RELATED APPLICATIONS

This application claims priority from U.S. Provisional Application No. 60/219,080 filed Jul. 18, 2000.

FIELD OF THE INVENTION

The present invention relates to a process for manufacturing fatty acid nitrites and fatty amines by the cross-metathesis of normal alpha olefins and acrylonitrile in the presence of an organometallic cross-metathesis catalyst.

BACKGROUND OF THE INVENTION

Fatty amines are commercially valuable products which have various commercial uses, such as, in the manufacture of surfactants and soaps. An economically attractive method for making these products from olefins would be highly desirable. A process for the metathesis of olefins is taught in U.S. Pat. No. 4,681,956 using an organo-metallic catalyst containing a molybdenum or tungsten ligand complex. Similar catalysts that have been shown to be useful in the metathesis of olefins are also described in U.S. Pat. No. 5,146,033. The catalysts described in the aforesaid US Patents are usually referred to as Schrock catalysts. U.S. Pat. No. 5,175,370 describes a method for converting a fatty acid nitrile into a fatty amine. The hydrogenation of fatty nitriles to primary fatty amines is also described in U.S. Pat. No. 3,574,754.

Crowe et al. in "Acrylonitrile Cross Metathesis: Coaxing Olefin Metathesis Reactivity from a Reluctant Substrate", J. Am. Chem. Soc., 117, 5162–5163 (1995) describes a method for the cross metathesis of acrylonitrile and normal alpha olefins to produce alkenylcyanides using a Schrock catalyst. Crowe et al.'s method has the advantage over previous methods of preparing unsaturated nitriles from n-alpha olefins of having high selectivity, i.e., minimizing the side reactions which reduce the yield of the desired fatty acid nitrile product. A major disadvantage of the process route described in Crowe et al. for the commercial production of unsaturated nitrites is the loss of the catalyst during processing. The Schrock catalyst used in the Crowe et al. method is expensive, and prior to the present invention, it has not been possible to immobilize the catalyst without affecting the cross-metathesis activity of the catalyst. Without some method for economically recovering the catalyst from the reaction mixture or for immobilizing the catalyst during the metathesis step, this route is commercially impractical.

SUMMARY OF THE INVENTION

One embodiment of the present invention is directed to a process for making a saturated fatty amine or saturated fatty diamine having a general structure according to the following formula:

R—CH$_2$—CH$_2$—CH$_2$—NR'R"

wherein
R represents methyl or an alkyl moiety of the general formula CH$_3$—(CH$_2$)$_n$— wherein n equals an integer of from 1 to about 18;
or alternatively R represents an alkyl amine moiety of the general formula NH$_2$—CH$_2$—CH$_2$—(CH$_2$)$_m$— wherein m equals an integer of from 2 to about 17;
and R' and R" independently represent hydrogen, alkyl, alkylaryl, aryl, haloalkyl, haloalkylaryl, or haloaryl;
said process comprising:
(a) contacting a feed with acrylonitrile in the presence of an organometallic cross-metathesis catalyst for a time and under conditions preselected to promote cross-metathesis, said feed comprising at least one of a compound selected from the group consisting of a normal alpha olefin having from three to about twenty-one carbon atoms and an olefin of the general formula CH$_2$=CH—(CH$_2$)$_x$—CH=CH$_2$ wherein x is an integer of from 1 to about 16, whereby either the corresponding alkenylcyanide intermediate or bis alkenylcyanide intermediate, respectively, is formed;
(b) hydrogenating the alkenylcyanide intermediate or bis alkenylcyanide intermediate of step (a) in the presence of a hydrogenation catalyst and in the presence of an amine of the general formula HNR'R" under hydrogenation conditions sufficient to convert the intermediate to the corresponding saturated fatty amine or saturated fatty diamine of the general formula R—CH$_2$—CH$_2$—CH$_2$—NR'R"; and
(c) recovering the saturated fatty amine or fatty diamine of step (b).

As used herein, R' and R" when they are other than hydrogen represent a hydrocarbon moiety which will usually contain from 1 to about 30 carbon atoms in the structure. The prefix "halo-" indicates the presence of a halogen substitution, i.e., the substitution of a fluorine, chlorine, bromine, or iodine atom for one or more hydrogen atoms that would otherwise be present in said moiety.

The alkenylcyanide intermediate referred to above is a fatty acid nitrile having the following general formula:

A—CH=CH—CN wherein A represents methyl or an alkyl moiety of the general formula CH$_3$—(CH$_2$)$_n$— wherein n equals an integer of from 1 to 18. It should be noted that the unsaturated carbon to carbon bond is always located next to the cyano moiety.

The bis alkenylcyanide intermediate would have the same general formula as the alkenylcyanide intermediate; however, in this instance, A would represent an alkyl amine moiety of the general formula NC—CH=CH—(CH$_2$)$_y$— wherein y equals an integer of from 2 to 16.

In the preferred embodiment of the invention, the organometallic cross-metathesis catalyst is immobilized and reused to catalyze additional cross-metathesis reactions. It has been found that a particularly advantageous method for immobilizing the cross metathesis catalyst is by dissolving the catalyst in an aprotic ionic liquid. Accordingly, another embodiment of the present invention is directed to a process for making an alkenylcyanide or bis alkenylcyanide characterized by the general formula:

A—CH=CH—CN wherein
A represents methyl or an alkyl moiety of the general formula CH$_3$—(CH$_2$)$_n$— wherein n equals an integer of from 1 to 18;
or alternatively A represents an alkyl amine moiety of the general formula NC—CH=CH—(CH$_2$)$_y$— wherein y equals an integer of from 2 to 16;
said process comprising the steps of:
(a) contacting in a cross-metathesis zone an organic phase with a ionic liquid phase comprising an organometallic cross-metathesis catalyst and an aprotic ionic liquid under reaction conditions and for a time preselected to promote cross-metathesis, said organic phase comprising a mixture of an organic solvent, acrylonitrile, and one or more compounds selected from the group consisting of a normal alpha olefin having from three to about twenty-one carbon atoms and an olefin of the general formula $CH_2=CH-(CH_2)_x-CH=CH_2$ wherein x is an integer of from 1 to 16; and (b) recovering from the cross-metathesis zone a cross-metathesis product consisting of an alkenylcyanide or bis alkenylcyanide from the organic phase.

The catalyst used in carrying out the cross-metathesis of the normal acrylonitrile with a normal olefin is broadly referred to as an organometallic cross-metathesis catalyst. Such catalysts contain an organometallic ligand usually containing a metal selected from tungsten, molybdenum, ruthenium, rhenium, and rhodium. The preferred catalysts for carrying out the cross-metathesis is a Schrock catalyst. As used herein, a Scrock catalyst means a catalyst as generally described in U.S. Pat. No. 4,681,956 and 5,146,033, the contents of both patents being herein incorporated by reference. Particularly useful as catalysts in the cross-metathesis reactions of the present invention are those Schrock catalysts having the following general formula:

$$M(NR^1)(OR^2)_2CHR^3)$$

wherein M is molybdenum or tungsten, and more preferably molybdenum; $R^1$ is alkyl, aryl, or arylalkyl; $R^2$ is alkyl, aryl, arylalkyl or halogen substituted derivatives thereof, particularly preferred is a fluorinated alkyl or fluorinated aryl; and $R^3$ is alkyl, aryl, or arylalkyl.

Particularly preferred are those Schrock catalysts containing molybdenum. Especially preferred as a catalyst is 2,6-diisopropylphenylimidoneophylidenemolybdenum (VI) bis (hexafluoro-t-butoxide) which has been successfully used to carry out the cross-metathesis step according to the present invention.

In a preferred embodiment of the present invention, the organometallic cross-metathesis catalyst is dissolved in an aprotic ionic liquid solvent. Ionic liquids, as referred to herein, are primarily salts or mixtures of salts which melt below room temperature. Aprotic ionic liquids used in carrying out this invention may be characterized by the general formula $Q^+ A^-$, wherein $Q^+$ is quaternary ammonium, quaternary phosphonium, or quaternary sulfonium, and $A^-$ is an unreactive negatively charged ion such as $PF_6^-$. The aprotic ionic liquid 1-butyl-3-methylimidazolium hexafluorophosphate has been used successfully as a solvent for the Schrock catalyst in practicing the present invention.

In carrying out the cross-metathesis step, the acrylonitrile and olefin are contacted with a catalytically effective amount of the organometallic cross-metathesis catalyst. As used herein, the phrase "catalytically effective amount" refers an amount of catalyst sufficient to promote the cross-metathesis of the acrylonitrile and olefin. The catalytically effective amount may vary depending on the particular organometallic cross-metathesis catalyst selected; however, the determination of the amount of catalyst necessary to promote the cross-metathesis reaction should require no more than routine testing which is well within the skill of one familiar with the science of catalysis.

Another advantage of the process of the present invention is that the cross-metathesis step will readily proceed at or near room temperature. In addition to the desired alkenylcyanide and bis alkenylcyanide products of the cross-metathesis step, some by-products may be produced. These by-products may be sent to a separate metathesis zone for conversion back into the corresponding olefin and recycled back to the cross-metathesis reaction zone. Alternatively, the by-products may be recycled directly back to the cross-metathesis reaction zone for conversion in-situ.

As used in this disclosure, the words "comprises" or "comprising" is intended as an open-ended transition meaning the inclusion of the named elements, but not necessarily excluding other unnamed elements. The phrase "consists essentially of" or "consisting essentially of" is intended to mean the exclusion of other elements of any essential significance to the combination. The phrase "consisting of" is intended as a transition meaning the exclusion of all but the recited elements with the exception of only minor traces of impurities.

DETAILED DESCRIPTION OF THE INVENTION

The present invention provides a practical and economic method for producing an alkenylcyanide or bis alkenylcyanide intermediate which may be readily converted by hydrogenation into the corresponding fatty amine. The general cross-metathesis reaction between a normal alpha olefin feedstock and acrylonitrile may be represented as follows:

$$A-CH=CH_2+CH_2=CHCN \rightarrow A-CH=CHCN+CH_2=CH_2$$

wherein A represents the same moiety as stated above.

In addition to the alkenylcyanide, the cross-metathesis may produce a significant amount of an undesired internal olefin of the general formula:

$$A-CH=CH-A$$

Although usually not favored, some 1,2-dicyanoethylene may also be produced as an undesired by-product. This by-product is usually not produced in significant amounts and, as such, does not represent a problem in obtaining good yields of the desired products. The Schrock catalysts are preferred in the cross-metathesis reaction, because it has been found that the Schrock catalysts minimize the occurrence of the side reactions which produce these undesired products. This is more fully explained in the article titled "Acrylonitrile Cross Metathesis: Coaxing Olefin Metathesis Reactivity from a Reluctant Substrate" by Crowe et al., J. Am. Chem. Soc., 117, 5162–5163 (1995), the entire contents of which are herein incorporated by reference.

The corresponding cross-metathesis reaction between acrylonitrile and an olefin having unsaturated bonds at both ends of the chain may be represented by the following general reaction:

$$CH_2=CH-(CH_2)_x-CH=CH_2+2CH_2=CHCN \rightarrow NCCH=CH-(CH_2)_x-CH=CHCN+2CH_2=CH_2$$

wherein x represents the same integers as defined above.

In both the production of the alkenylcyanide and the bis alkenylcyanide, an additional product of the cross-metathesis reaction is ethylene. Ethylene is a starting material for a number of useful products, including polyethylene. Thus, ethylene may optionally be recovered as a usable by-product or alternatively may be used as a fuel gas.

While other organometallic cross-metathesis catalysts may be operable, a Schrock catalyst is generally preferred to promote the cross-metathesis reaction. A Schrock catalyst contains an organometallic ligand containing a metal such as molybdenum, tungsten, or rhenium, with molybdenum or tungsten being preferred and molybdenum being particularly preferred. As noted above, the Schrock catalysts used in carrying out the cross-metathesis step may be represented by the general formula:

$$M(NR^1)(OR^2)_2CHR^3)$$

wherein M, $R^1$, $R^2$, and $R^3$ are the same as defined above.

Preferred Schrock catalysts include those in which $R^1$ and $R^2$ represent halogen substituted alkyls, especially fluorinated alkyls. During the cross-metathesis reaction, the $CHR^3$ moiety is disassociated from the active site at which the cross-metathesis occurs. Therefore, this moiety should be one which readily disassociates from the rest of the molecule under the conditions of the cross-metathesis reaction. Tertiary butyl, phenyl, or substituted phenyl are generally preferred for $R^3$. Particularly preferred as a catalyst is 2,6-diisopropylphenylimidoneophylidenemolybdenum (VI) bis(hexafluoro-t-butoxide) which has been shown to readily catalyze the cross-metathesis reaction.

In carrying out the cross-metathesis step, the organometallic cross-metathesis catalyst is preferably immobilized so that it can be recovered and recycled. Methods for immobilizing a catalyst are well known to those skill in the art. For example, the catalyst may be immobilized on a support such as on a silica or a silica-alumina support. Other supports include, but are not necessarily limited to polymers such as polystyrene beads, natural occurring materials such as clays or diatomaceous earth, or other inert materials such as for example charcoal. However, any support should be such that it does not hinder the catalytic activity of the organometallic cross-metathesis catalyst. In the case of a Schrock catalyst, it has been found advantageous to dissolve the catalyst in an aprotic ionic liquid. This effectively immobilizes the Schrock catalyst while not interfering with the ability of the catalyst to promote the cross-metathesis reaction. In addition, since the products of the cross-metathesis are not soluble in the ionic liquid medium, the separation is relatively easy.

As discussed above, an aprotic ionic liquid refers to a salt or mixture of salts that is normally liquid at room temperature. The aprotic ionic liquid 1-butyl-3-methylimidazolium hexafluorophosphate has been used successfully as a solvent for the Schrock catalyst in practicing the present invention and represents a preferred embodiment.

In carrying out the cross-metathesis reaction, the ionic liquid/Schrock catalyst forms one phase in the metathesis zone. The acrylonitrile and olefin form a separate organic phase. Usually an organic solvent will be also present as part of the organic phase. Organic solvents suitable for use in dissolving the normal olefin and the acrylonitrile are well known to those in the art. Examples of organic solvents useful in the present invention include lower molecular weight alkanes which are liquid at room temperature, such as, for example, pentane or hexane; ethers such as diethyl ether; aromatic hydrocarbons such as toluene; halide substituted alkanes, such as, for example, dichloromethane; and the like. In selecting the solvent, it should readily dissolve both the acrylonitrile and the olefin, but obviously it should not dissolve or dissolve into the ionic liquid. In addition, it is usually desirable that the organic phase solvent also dissolve the alkenyl cyanide or bis alkenylcyanide products to facilitate separation. However, in certain instances, it may be possible to collect the products as a precipitate.

The cross-metathesis reaction will usually proceed at room temperature, so little or no heating of the reaction mixture is required. Usually, the reaction mixture will be vigorously stirred for a time sufficient to allow the cross-metathesis reaction to reach equilibrium after which the stirring is stopped, and two phases are allowed to separate. The Schrock catalyst will remain as part of the ionic liquid phase while the alkenyl cyanide or bis alkenylcyanide products, ethylene, and any by-products will remain in the organic phase. Thus, the Schrock catalyst may be readily recovered as part of the ionic liquid phase and recycled for use in additional cross-metathesis reactions with fresh feed. The alkenylcyanide or bis alkenylcyanide products may be recovered from the organic phase for use as intermediates in the preparation of fatty amines as explained below or for the production of other end products.

As noted above, the alkenylcyanide and bis alkenylcyanide may serve as intermediates in the manufacture of saturated fatty amines. The hydrogenation of an alkenylcyanide to the corresponding fatty amine is disclosed in U.S. Pat. Nos. 3,574,754 and 5,175,370. The hydrogenation of the alkenylcyanide or bis alkenylcyanide intermediates is carried out in the presence of a hydrogenation catalyst such as, for example, one containing nickel, palladium, platinum, cobalt or the like. Although in U.S. Pat. No. 5,175,370 the hydrogenation of the alkenylcyanide to the fatty amine is carried out as two separate steps, in the present invention, the hydrogenation of both the unsaturated carbon to carbon bond and nitrile group would occur as a single step.

In general, the hydrogenation step is carried at an elevated temperature of between about 50° C. and 200° C., with a temperature between about 110° C. and about 150° C. being preferred. The pressure in the hydrogenation zone is super atmospheric and will usually fall within the range of from about 500 to about 1100 psi, with a pressure in the range from about 500 to about 700 psi being preferred. Hydrogen must be available in the hydrogenation zone in excess of the stoichiometric amount required to saturate the nitrile groups present in order to force the reaction to completion. An amine having the general formula HNR!R" should also be present in the reaction zone. Of course, when both R' and R" are hydrogen, the amine is ammonia. The presence of ammonia prevents the formation of undesirable secondary and tertiary amines and should be present in the range of from about 0.5 to about 8 moles or more per mole of nitrile, with the preferred range being between about 1.5 to about 2 moles of ammonia. When R' and/or R" are other than hydrogen, these moieties provide the appropriate N substitution of the desired fatty amine product.

EXAMPLES

The following specific examples are intended to be illustrative of the invention; however, they should not be construed as a limitation on the scope of the invention.

Example 1

The reagents 1-octene and acrylonitrile and the solvent hexane were dried over 4 Å molecular sieves for 48 hours, degassed, and placed in an inert atmosphere glove box. In the glove box, 100 mg (0.13 mmol) of 2,6-diisopropylphenylimido-neophylidenemolybdenum (VI) bis (hexafluoro-t-butoxide) (Schrock's catalyst: Strem catalog #42-1205) was mixed with 3 mL of the ionic liquid 1-butyl-3-methylimidazolium hexafluorophosphate (bmim$^+$PF$_6^-$) in a dried 20 mL vial. This catalyst/ionic liquid solution was stirred vigorously for 20 minutes. In another 20 mL vial, 0.10 mL (0.65 mmol ) of 1-octene and 0.12 mL (1.9 mmol) of acrylonitrile were added to 3 mL of hexane to form an organic solution. The organic solution was then added to the vial containing the ionic liquid/catalyst solution. The resulting reaction mixture was stirred at room temperature for 3 hours. The organic layer was decanted from the reaction mixture and analyzed by gas chromatography (GC) and gas chromatography/mass spectroscopy (GC/MS). The analysis of the organic layer indicated the formation of the cross-metathesis product cis/trans-1-nonanitrile and the self-metathesis product cis/trans-7-tetradecene.

Example 2

In the glove box, 150 mg (0.20 mmol) of 2,6-diisopropylphenylimido-neophylidenemolybdenum (VI) bis(hexafluoro-t-butoxide) (Schrock's catalyst) was added to 4 mL of the ionic liquid 1-butyl-3-methylimidazolium hexafluorophosphate (bmim$^+$PF$_6^-$) in a dried 20 mL vial. This ionic liquid/catalyst solution was stirred vigorously for 40 minutes. In another 20 mL vial, 0.5 mL (3.2 mmol) of 1-octene and 0.5 mL (7.6 mmol) were added to 8 mL of hexane. The ionic liquid/catalyst solution was decanted to remove undissolved catalyst. Half of the organic reagents solution was added to the decanted ionic liquid. The reaction was stirred at room temperature for 2.5 hours. The organic layer was decanted from the reaction so that only the ionic liquid layer remained. The other half of organic reagents solution was then added to the ionic liquid layer. This reaction was stirred at room temperature for 3 hours and then the organic layer was removed. Both organic layers were analyzed by GC and GC/MS. In both organic layers, the cross-metathesis product cis/trans-1-nonanitrile and the self-metathesis product cis-trans-7-tetradecene were detected. This experiment indicates that some Schrock's catalyst remained dissolved in the ionic liquid layer. The reaction also indicates that the catalyst is effectively immobilized in the ionic liquid layer since the ionic liquid layer shows catalytic activity in consecutive batch reactions demonstrating the ability to recover and recycle the catalyst.

Example 3

The hydrogenation of an alkenylcyanide to the corresponding fatty amine was demonstrated by charging a one-liter autoclave with 24.4 grams of 1-heptenecyanide [CH$_3$(CH$_2$)$_4$HC=CHCN], 3 grams of hydrogenation catalyst (60% nickel on silica gel obtained from Aldrich), and 200 ml of a 2.0 molar solution of ammonia in methanol. The autoclave was evacuated and purged three times with nitrogen after which the autoclave was pressurized to 400 psi with hydrogen. The reaction mixture was stirred and the temperature raised to 125° C. The pressure in the autoclave was maintained with hydrogen at between 350 and 400 psi. After 2 hours, the reaction was stopped, the reaction mixture was filtered, and the contents analyzed by gas chromatography. Analysis showed 25.85 grams of octylamine and no remaining nitrile.

What is claimed is:

1. A process for making a saturated fatty amine or saturated fatty diamine having a general structure according to the following formula:

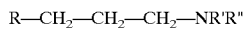

wherein

R represents methyl or an alkyl moiety of the general formula CH$_3$—(CH$_2$)$_n$— wherein n equals an integer of from 1 to about 18;

or alternatively R represents an alkyl amine moiety of the general formula NH$_2$—CH$_2$—CH$_2$—(CH$_2$)$_m$ wherein m equals an integer of from 2 to about 17; and R' and R" independently represent hydrogen, alkyl, alkylaryl, aryl, haloalkyl, haloalkylaryl, or haloaryl;

said process comprising:

(a) contacting a feed with acrylonitrile in the presence of an organometallic cross-metathesis catalyst for a time and under conditions preselected to promote cross-metathesis, said feed comprising at least one of a compound selected from the group consisting of a normal alpha olefin having from three to about twenty-one carbon atoms and an olefin of the general formula CH$_2$=CH—(CH$_2$)$_x$—CH=CH$_2$ wherein x is an integer of from 1 to about 16, whereby either the corresponding alkenylcyanide intermediate or bis alkenylcyanide intermediate, respectively, is formed;

(b) hydrogenating the alkenylcyanide intermediate or bis alkenylcyanide intermediate of step (a) in the presence of a hydrogenation catalyst and in the presence of an amine of the general formula HNR'R" under hydrogenation conditions sufficient to convert the intermediate to the corresponding saturated fatty amine or saturated fatty diamine of the general formula R—CH$_2$—CH$_2$—CH$_2$—NR'R"; and (c) recovering the saturated fatty amine or fatty diamine of step (b).

2. The process of claim 1 wherein the feed comprises a normal alpha olefin having from three to about twenty one carbon atoms and the corresponding saturated fatty amine recovered in step (c) contains from four to about twenty-two carbon atoms.

3. The process of claim 2 wherein the normal alpha olefin in the feed has from about 11 to about 17 carbon atoms and the corresponding saturated fatty amine contains from about 12 to about 18 carbon atoms.

4. The process of claim 1 wherein the feed comprises an olefin of the general formula:

wherein x is an integer of from 1 to about 16 and the corresponding saturated fatty diamine is characterized by the general formula:

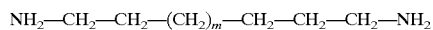

wherein m equals an integer of from 2 to about 17.

5. The process of claim 1 wherein the organometallic cross-metathesis catalyst is a Schrock catalyst.

6. The process of claim 5 wherein the Schrock catalyst contains molybdenum or tungsten.

7. The process of claim 6 wherein the metal is molybdenum.

8. The process of claim 7 wherein the Schrock catalyst is 2,6-diisopropylphenylimidoneophylidenemolybdenum (VI) bis(hexafluoro-t-butoxide).

9. The process of claim 1 wherein the organometallic cross metathesis catalyst is immobilized.

10. The process of claim 9 wherein the organometallic cross-metathesis catalyst is immobilized in a aprotic ionic liquid.

11. A process for making an alkenylcyanide or bis alkenylcyanide characterized by the general formula:

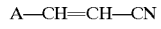

wherein

A represents methyl or an alkyl moiety of the general formula CH$_3$—(CH$_2$)$_n$— wherein n equals an integer of from 1 to 18, or alternatively A represents an alkyl amine moiety of the general formula:

NC—CH=CH—(CH$_2$)$_y$— wherein y equals an integer of from 2 to 16;
said process comprising the steps of:
(a) contacting in a cross-metathesis zone an organic phase with a ionic liquid phase comprising an organometallic cross-metathesis catalyst and a aprotic ionic liquid under reaction conditions and for a time preselected to promote cross-metathesis, said organic phase comprising a mixture of an organic solvent, acrylonitrile, and one or more compounds selected from the group consisting of a normal alpha olefin having from three to about twenty-one carbon atoms and an olefin of the general formula:

CH$_2$=CH—(CH$_2$)$_x$—CH=CH$_2$ wherein x is an integer of from 1 to 16; and
(b) recovering from the cross-metathesis zone a cross-metathesis product consisting of an alkenylcyanide or bis alkenylcyanide from the organic phase.

12. The process of claim 11 wherein the organic phase contains a normal alpha olefin of from three to about twenty-one carbon atoms and the cross-metathesis product comprises the corresponding alkenylcyanide.

13. The process of claim 12 wherein the normal alpha olefin in the organic phase has from about 11 to about 17 carbon atoms.

14. The process of claim 12 wherein the alkenylcyanide is hydrogenated to the corresponding fatty amine.

15. The process of claim 11 wherein the organic phase contains an olefin of the general formula CH$_2$=CH—(CH$_2$)$_x$—CH=CH$_2$ wherein x is as defined above and the cross-metathesis product comprises the corresponding bis alkenylcyanide.

16. The process of claim 12 wherein the cross metathesis product also includes an internal olefin of the general formula A—CH=CH—A.

17. The process of claim 16 wherein the internal olefin is contacted with a metathesis catalyst in a metathesis zone under metathesis conditions to produce a normal alpha olefin.

18. The process of claim 17 wherein the normal alpha olefin is recovered from the metathesis zone and is recycled to the cross-metathesis zone.

19. The process of claim 16 wherein the internal olefin is recycled directly to the cross-metathesis zone.

20. The process of claim 11 wherein the organometallic cross-metathesis catalyst is a Schrock catalyst.

21. The process of claim 20 wherein the Schrock catalyst contains molybdenum or tungsten.

22. The process of claim 21 wherein the metal is molybdenum.

23. The process of claim 22 wherein the Schrock catalyst is 2,6-diisopropylphenylimidoneophylidenemolybdenum (VI) bis(hexafluoro-t-butoxide).

24. The process of claim 11 wherein the aprotic ionic liquid is 1-butyl-3-methylimidazolium hexafluorophosphate.

25. The process of claim 11 wherein the cross metathesis reaction is carried out at a temperature between about 15° C. and about 50° C.

* * * * *